US012648751B2

(12) United States Patent
    Curtis

(10) Patent No.: US 12,648,751 B2
(45) Date of Patent: Jun. 9, 2026

(54) ELECTRONIC STETHOSCOPE WITH A SONOGRAM

(71) Applicant: Wilson Curtis, Charlotte, NC (US)

(72) Inventor: Wilson Curtis, Charlotte, NC (US)

( * ) Notice: Subject to any disclaimer, the term of this patent is extended or adjusted under 35 U.S.C. 154(b) by 350 days.

(21) Appl. No.: 18/467,181

(22) Filed: Sep. 14, 2023

(65) Prior Publication Data

US 2024/0138805 A1      May 2, 2024

Related U.S. Application Data

(60) Provisional application No. 63/420,835, filed on Oct. 31, 2022.

(51) Int. Cl.
    *A61B 7/04*          (2006.01)
    *A61B 8/00*          (2006.01)

(52) U.S. Cl.
    CPC ............. *A61B 7/04* (2013.01); *A61B 8/4427* (2013.01)

(58) Field of Classification Search
    CPC .... A61B 7/02; A61B 7/04; A61B 8/00; A61B 8/02; A61B 8/0883
    See application file for complete search history.

(56) References Cited

U.S. PATENT DOCUMENTS

| | | | |
|---|---|---|---|
| 5,389,747 A * | 2/1995 | Mohrin | ..................... A61B 7/02 |
| | | | 181/131 |
| 5,960,089 A | 9/1999 | Bouricius | |
| 11,026,654 B2 | 6/2021 | Friedman | |
| 2005/0165310 A1* | 7/2005 | Bindefeld | ................ A61B 7/02 |
| | | | 600/453 |
| 2013/0116584 A1* | 5/2013 | Kapoor | ..................... A61B 5/02 |
| | | | 600/513 |
| 2020/0029837 A1* | 1/2020 | Joudi | ........................ A61B 7/04 |
| 2023/0120859 A1* | 4/2023 | Ting | ......................... A61B 7/02 |
| | | | 181/131 |

FOREIGN PATENT DOCUMENTS

KR          20110047181 A        5/2011

* cited by examiner

*Primary Examiner* — Chu Chuan Liu
(74) *Attorney, Agent, or Firm* — Rachel Mobley; Aminah Ghaffar; NCCU School of Law IP Clinic

(57)          ABSTRACT

An electronic stethoscope with a method of listening to sounds made by a heart, a lung, or blood flow along with using soundwaves transmitted from a transducer to observe a person's circulatory system wirelessly displayed onto a nearby monitor without switching devices.

12 Claims, 6 Drawing Sheets

ELECTRONIC STETHOSCOPE WITH A SONOGRAM

CROSS-REFERENCE TO RELATED APPLICATIONS

This application claims the benefit of U.S. Provisional Application No. 63/420,835, filed on Oct. 31, 2022, which is hereby incorporated in its entirety.

FIELD OF THE INVENTION

The present invention is directed to a stethoscope with a sonogram built into a chestpiece of a diaphragm that will provide the capabilities of both a stethoscope and a sonogram. Furthermore, the chestpiece comprises a transmitter configured to send data received by the chestpiece to an external display.

BACKGROUND

The following description is not an admission that any of the information provided herein is prior art or relevant to the present invention, or that any publication specifically or implicitly referenced is prior art. Any publications cited in this description are incorporated by reference herein. Where a definition or use of a term in an incorporated reference is inconsistent or contrary to the definition of that term provided herein, the definition of that term provided herein applies and the definition of that term in the reference does not apply.

Ensuring healthy lives and promoting well-being is a major concern everywhere in our world. For example, a major issue in the United States is reducing the number of fatalities due to cardiovascular or heart disease. Cardiovascular or heart disease affects the lives of millions of people and may affect the health of a patient without warning. In particular, detection of these diseases typically involves evaluating a patient's history, performing a physical examination, stress testing, blood tests, and a coronary angiogram on the patient as well. An evaluation of a patient's history and/or performing a physical evaluation, however, may not provide enough information for a confident conclusion. Although stress testing is normally ordered to detect possible heart problems, the specificity and sensitivity of the stress test varies greatly depending on if the disease is single or multi-vessel. Furthermore, the coronary angiogram procedures are invasive and carry substantial cost and/or unnecessary risk to the patient.

Therefore, there exists a need for a device that does not have the aforementioned limitations and provides health professionals the convenience of not having to conduct various tests on patients. Also, there exists a need for a device to help prolong the life of the patients by decreasing the chances of having a stroke, heart attack, or organ failure by detecting signs weeks or months before issues occur.

SUMMARY OF THE INVENTION

The present invention is directed to a stethoscope with a sonogram built into a chestpiece on the stethoscope. The invention allows users to see and hear the circulatory system by sending soundwaves from a transducer inside the chestpiece that echo back and are transmitted to an external display. This process helps the user catch and diagnose infections, diseases, clots, and irregular blood flow in patients before any issues occur. The user can also use this device as a stethoscope during patient check-ups. Furthermore, if the user hears something wrong with the 10 patient or the patient's medical file indicates something is wrong, the user can make a more accurate diagnosis without having to conduct various tests.

In one embodiment, an electronic stethoscope comprises: a pair of ear tubes; tubing; a binaural spring; and a chestpiece, wherein said chestpiece comprises: a bell; a drum; a diaphragm located on a bottom side of the chestpiece; a stem; a circuit board; and a housing, wherein: the bell is connected to a top end of the drum; the stem is attached to a curved side of the drum; a bottom end of the drum is connected to a top end of the housing; the housing comprises a transducer, wherein the transducer comprises a shield; the transducer is electrically interconnected to the circuit board; the circuit board comprises a battery and a transmitter, wherein the battery and the transmitter are electrically interconnected to the circuit board; the circuit board is connected to a top end of the shield; and the stem is connected to the tubing, wherein the binaural spring is connected to a bottom end of the pair of ear tubes; and the tubing envelops the bottom end of the pair of ear tubes and the binaural spring.

In a further embodiment, the diaphragm further comprises a plurality of soundwave holes located on the bottom side of the chestpiece. In still a further embodiment, the chestpiece is configured to: produce soundwaves from the transducer that are sent through the plurality of soundwave holes to a patient's skin; receive echoed soundwaves that are echoed off the patient's skin; and transmit the echoed soundwaves through the transmitter to a monitor.

In yet another embodiment, the transducer further comprises an acoustic insulator and a piezoelectric element. In a further embodiment, the ear tubes comprise a corresponding ear tip. In one embodiment, the transmitter is a Bluetooth transmitter. In a further embodiment, the chestpiece comprises a lens. In a further embodiment, the chestpiece comprises a switch, wherein the switch is configured to control power to the circuit board.

In another embodiment, a method of using an electronic stethoscope comprises: applying a gel on a patient's skin; producing soundwaves from a transducer, wherein the transducer is electrically connected to a circuit board and a battery located inside a chestpiece, wherein the soundwaves are sent to the patient's skin; receiving echoed soundwaves from the patient's skin; and transmitting the echoed soundwaves through a transmitter to a monitor, wherein the transmitter is electrically interconnected to the circuit board and the battery is located inside the chestpiece.

In a further embodiment, a bottom side of the chestpiece comprises a diaphragm and the diaphragm comprises a plurality of soundwave holes. In still a further embodiment, the soundwaves that are produced from the transducer pass through the plurality of soundwave holes before reaching the patient's skin.

In yet another embodiment, the transmitter is a Bluetooth transmitter. In a further embodiment, the chestpiece comprises a lens. In a further embodiment, the chestpiece comprises a switch, wherein the switch is configured to control power to the circuit board.

In a further embodiment, the electronic stethoscope further comprises: a pair of ear tubes; tubing; a binaural spring, wherein the chestpiece comprises: a bell; a drum; a stem; and a housing, wherein: the bell is connected to a top end of the drum; the stem is attached to a curved side of the drum; a bottom end of the drum is connected to a top end of the housing; the housing comprises a transducer, wherein the transducer comprises a shield; and the circuit board is connected to a top end of the shield, wherein: the stem is connected to the tubing; the binaural spring is connected to a bottom end of the pair of ear tubes; and the tubing envelops the bottom end of the pair of ear tubes and the binaural spring.

In one embodiment, an electronic stethoscope comprises: a pair of ear tubes; tubing; a binaural spring; and a chestpiece, wherein the chestpiece comprises: a bell; a drum; a diaphragm located on a bottom side of the chestpiece; a stem; a circuit board; and a housing, wherein: the bell is connected to a top end of the drum; the stem is attached to a curved side of the drum; a bottom end of the drum is connected to a top end of the housing; the housing comprises a transducer, wherein the transducer comprises a shield, an acoustic insulator, and a piezoelectric element; the transducer is electrically interconnected to the circuit board; the circuit board comprises a battery and a transmitter, wherein the battery and the transmitter are electrically interconnected to the circuit board; the circuit board is connected to a top end of the shield, and the diaphragm further comprises a plurality of soundwave holes located on the bottom side of the chestpiece, wherein: the stem is connected to the tubing; the binaural spring is connected to a bottom end of the pair of ear tubes; the ear tubes comprise a corresponding ear tip; and the tubing envelops the bottom end of the pair of ear tubes and the binaural spring.

In a further embodiment, the chestpiece is configured to: produce soundwaves from the transducer that are sent through the plurality of soundwave holes to a patient's skin; and receive echoed soundwaves that are echoed off the patient's skin; and transmit the echoed soundwaves through the transmitter to a monitor.

Various objects, features, aspects, and advantages of the inventive subject matter will become more apparent from the following detailed description of exemplary embodiments, along with the accompanying figures in which like numerals represent like components.

DETAILED DESCRIPTION

Before the invention is described in further detail, it is to be understood that the invention is not limited to the particular embodiments described, as such may, of course, vary. It is also to be understood that the terminology used herein is for the purpose of describing particular embodiments only, and not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of exemplary methods and materials are described herein.

As used in the description herein and throughout the claims that follow, the meaning of "a," "an," and "the" includes plural reference unless the context clearly dictates otherwise. Also, as used in the description herein, the meaning of "in" includes "into" and "on" unless the context clearly dictates otherwise.

Figure 1:
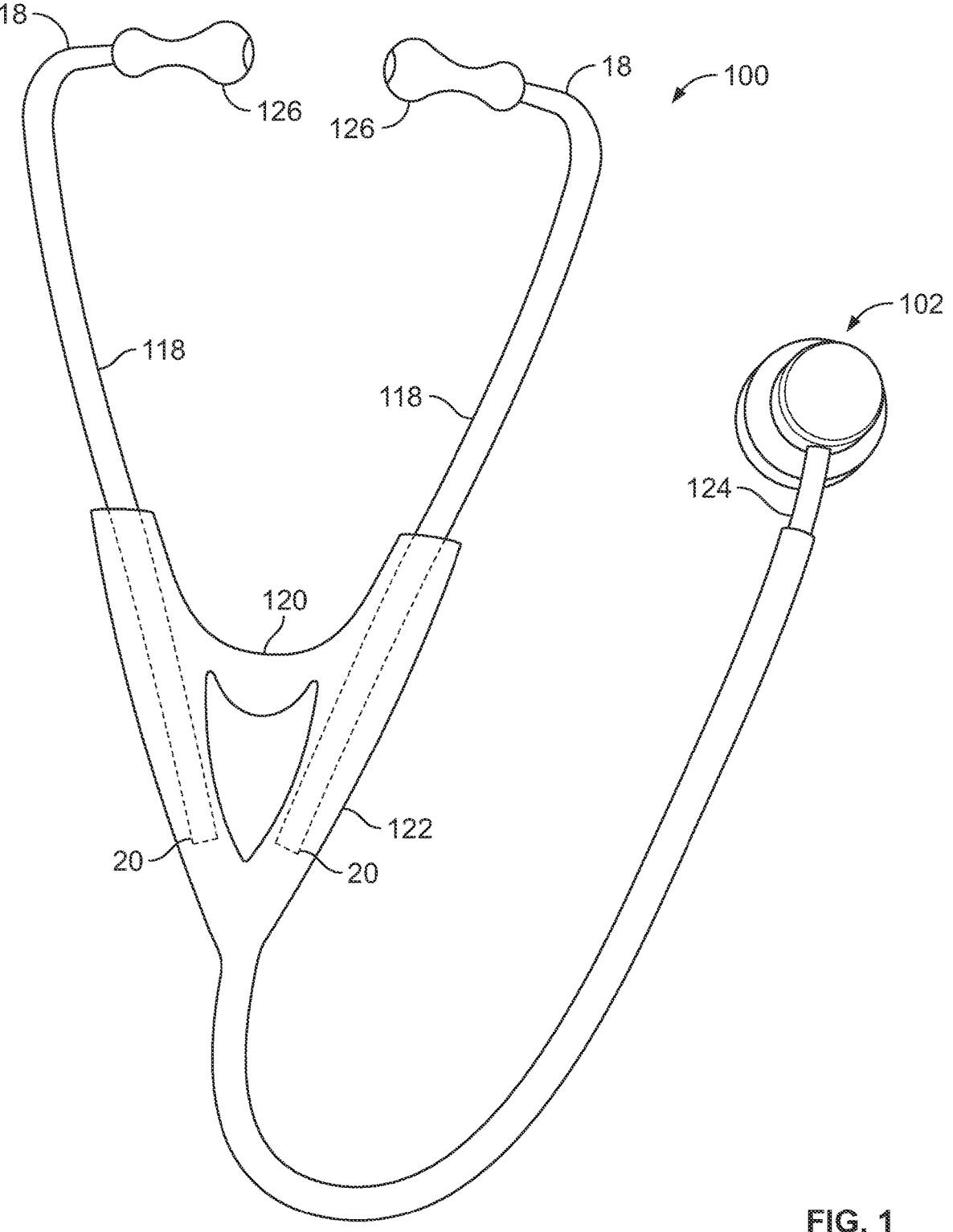
FIG. 1 is an exemplary configuration of a stethoscope.
Figure 2A:
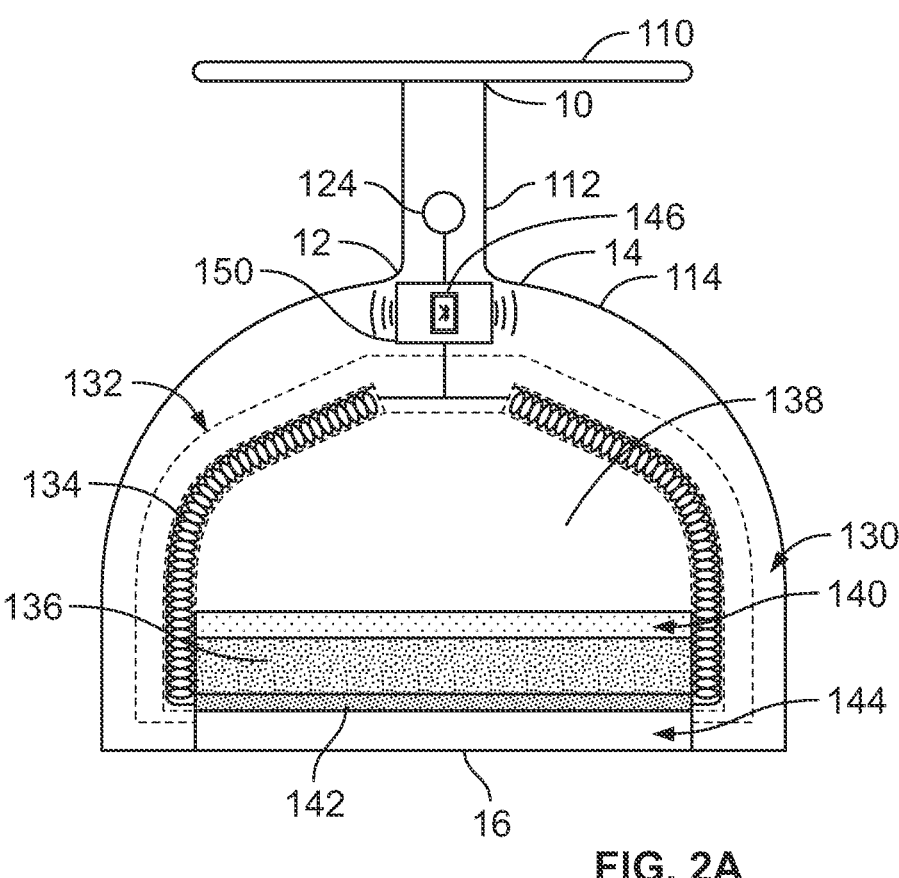
FIG. 2A is an exemplary configuration of a side view of an inner cross section of a chestpiece for the stethoscope.
Figure 3:
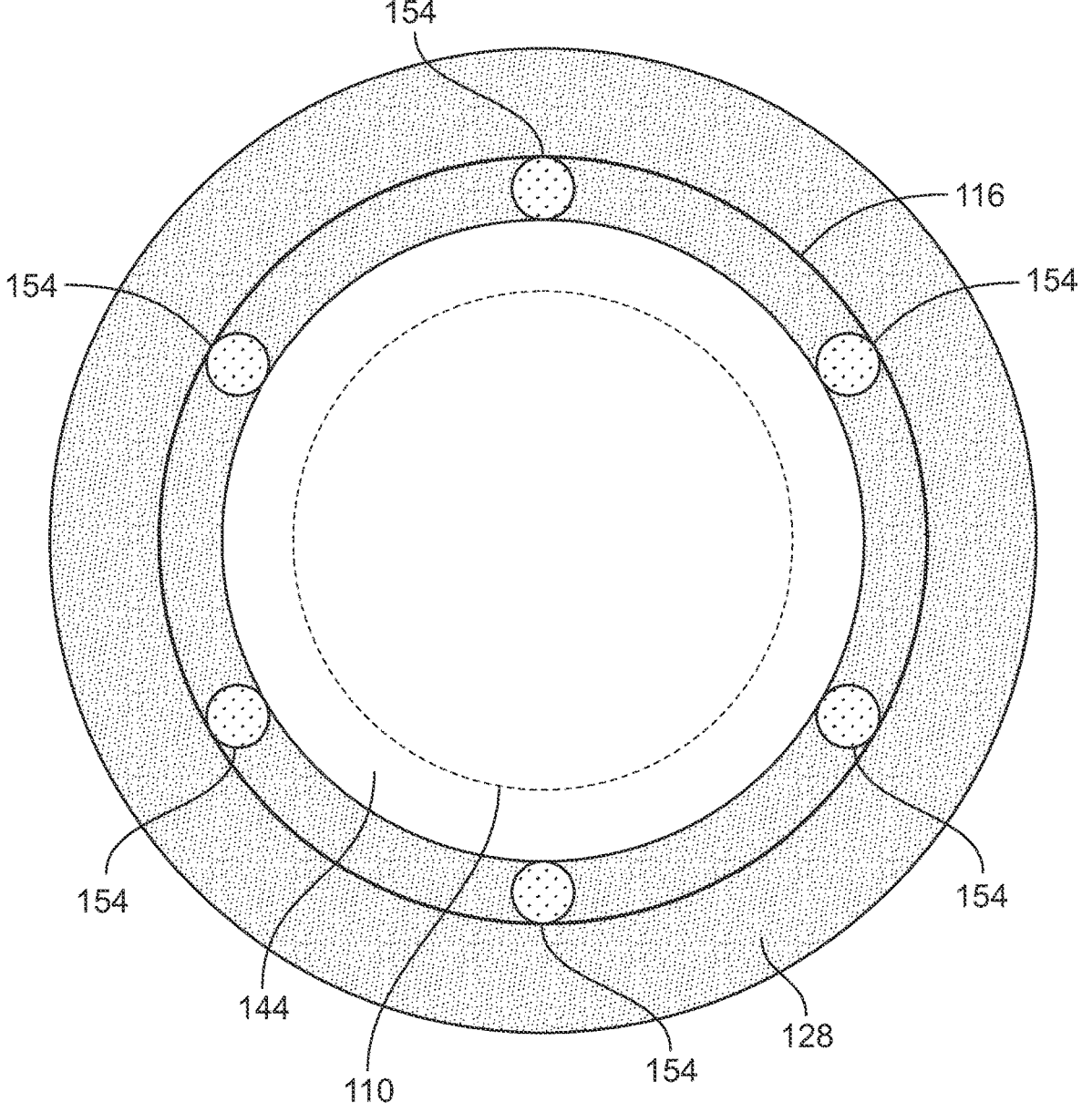
FIG. 3 is an exemplary configuration of a bottom view of the chestpiece.

FIG. 1 depicts an exemplary configuration of stethoscope 100 comprising ear tubes 118, binaural spring 120, tubing 122, and chestpiece 102. In an embodiment, stethoscope 100 comprises one or more ear tubes 118. In an embodiment, stethoscope 100 comprises two ear tubes 118. In an embodiment, each ear tube 118 comprises a corresponding ear tip 126, wherein each ear tip 126 is attached to top end 18 of each ear tube 118. In one embodiment, ear tubes 118 are connected to binaural spring 120. Tubing 122 envelops bottom end 20 of ear tubes 118 and binaural spring 120. Tubing 122 extends outwardly from bottom end 20 of ear tubes 118. FIG. 2A is an exemplary configuration of the inside of chestpiece 102. In one embodiment, chestpiece 102 comprises bell 110, drum 112, housing 114, diaphragm 116, as shown in FIG. 3, and stem 124. Bell 110 is connected to top end 10 of drum 112. Stem 124 is connected to a curved side of drum 112. In an embodiment, bottom end 12 of drum 112 is connected to top end 14 of housing 114. In an embodiment, tubing 122 is open, and hollow for stem 124 to be inserted into tubing 122. By connecting stem 124 to tubing 122, chestpiece 102 is attached to tubing 122. Bottom side 16 of chestpiece 102 is about a 4.3 cm diameter, while bell 110 at the top end of chestpiece 102 is about a 3.3 cm diameter.

Housing 114 may be made of aluminum, zinc, carbon fiber, copper, polystyrene (PE), polyvinyl chloride (PVC), or polypropylene (PP) but is not limited to these materials. In one embodiment, housing 114 is made of PE.

In an embodiment, housing 114 may comprise transducer 130. Transducer 130 comprises shield 132, acoustic insulator 134, piezoelectric element 136, damping block 138, positive electrode 140, ground electrode 142, and matching layer 144. In an embodiment, when chestpiece 102 touches a patient's skin, piezoelectric element 136 activates transducer 130 to begin transmitting sound waves out of chestpiece 102.

In an embodiment, shield 132 may be made of metal or plastic or any combination thereof. In one embodiment, shield 132 is made of metal.

In an exemplary embodiment, transducer 130 is configured to output sound waves from bottom side 16 of chestpiece 102. The sound waves bounce off the skin of a patient and send echoed soundwaves back to chestpiece 102 to show the inside of the patient's body. Furthermore, chestpiece 102 comprises transmitter 146, wherein transmitter 146 is configured to wirelessly transmit the echoed soundwaves produced from the soundwaves sent by transducer 130 to monitor 104. The transmitter 146 may be a Bluetooth transmitter, a Wi-Fi transmitter, or a combination thereof. In one embodiment, transmitter 146 is a Bluetooth transmitter. In one embodiment, monitor 104 is configured to wirelessly receive the echoed soundwaves from transmitter 146 and display the echoed soundwaves onto monitor 104. Furthermore, chestpiece 102 comprises battery 150, wherein battery 150 is capable of powering transmitter 146 and transducer 130. Battery 150 and transmitter 146 are electrically interconnected to circuit board 152. In other embodiments, chestpiece 102 comprises lens 156, shown in FIG. 5, attached to a bottom end of shield 132. Lens 156 may be different shapes including, but not limited to: concave, convex, or flat. By having different shapes for lens 156, the soundwaves produced by transducer 130 will output at different angles. In another embodiment, lens 156 is flat. Lens 156 may be made of cyclic olefin copolymer (COC), lead, glass, copper, steel, aluminum, or nickel but is not limited to these materials.

Figure 2B:
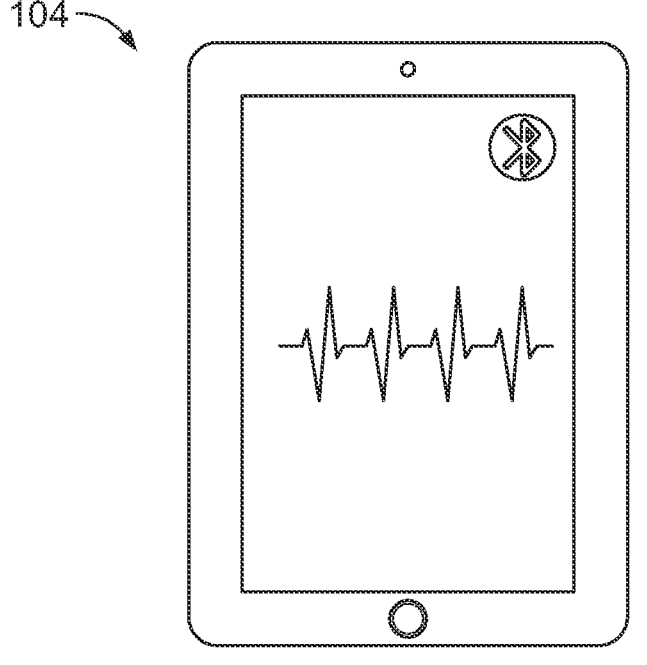
FIG. 2B is a view of a monitor wirelessly connected to the stethoscope.

FIG. 2B is an exemplary configuration of monitor 104 configured for displaying soundwaves transmitted from transmitter 146. Monitor 104 is capable of connecting to chestpiece 102 by, but not limited to, Bluetooth or Wi-Fi. In one embodiment, monitor 104 is connected to chestpiece 102 by Bluetooth. After monitor 104 is connected to chestpiece 102, transmitter 146 will transmit any echoed soundwaves from the soundwaves produced from transducer 130. In an embodiment, monitor 104 is electronically interconnected to a CPU or other known electric devices and also includes necessary software firmware and hardware for integrating with one or more monitors 104.

FIG. 3 depicts an embodiment of bottom side 16 of chestpiece 102, as depicted in FIG. 2A. Bottom side 16 comprises outer ring 128, matching layer 144 of transducer 130, and diaphragm 116. Outer ring 128 may be made of silicone, nitrile, vinyl, neoprene, or thermoplastic elastomers (TPE) but is not limited to these materials. In an embodiment, outer ring 128 is made of silicone.

In an embodiment outer ring 128 may comprise gel 148 that is released from outer ring 128 when outer ring 128 is pressed against a patient's skin. Gel 148 may be: 3B scientific W67051 sonigel, Roscoe medical LS5255, Aquasonic 100 Ultrasound Transmission Gel, or Parker 12-08 spectra but is not limited to these materials. In the present embodiment, gel 148 is Aquasonic 100 Ultrasound Transmission Gel. Gel 148 could be used for providing space between transducer 130 and the patient's skin. In an embodiment where outer ring 128 does not comprise gel 148, a user can manually apply gel 148 on the patient's skin. Gel 148 is configured to also allow the soundwaves produced from transducer 130 to travel to and from the patient's skin.

Diaphragm 116 comprises a plurality of soundwave holes 154. Diaphragm 116 may comprise any number of soundwave holes 154. In one embodiment, diaphragm 116 comprises six soundwave holes 154. When transducer 130 produces soundwaves, plurality of soundwave holes 154 are configured to help provide a greater frequency being produced from the soundwaves. Soundwave holes 154 may comprise a hydrophilic material such as, but not limited to, styrene acrylonitrile resin, addition-cured silicone, polyurethanes, polysulfide, polyvinyloxanether, or hydrocolloids. In an embodiment, plurality of soundwave holes 154 comprises a styrene acrylonitrile resin.

Figure 4:
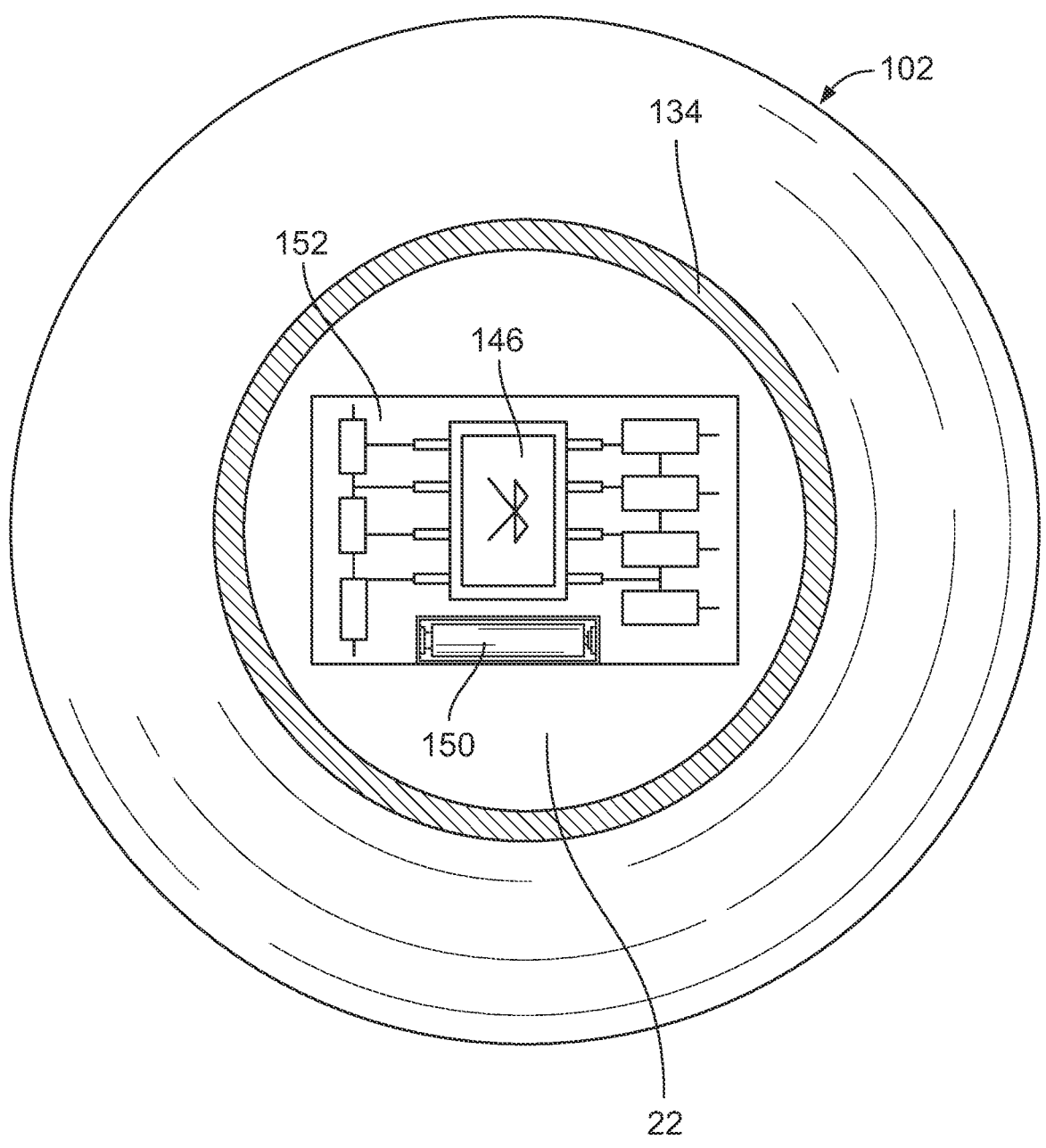
FIG. 4 is an exemplary configuration of a cross-sectional view of the chestpiece.

FIG. 4 is a cross-sectional view of chestpiece 102 depicting top end 22 of shield 132. In one embodiment, circuit board 152 is connected to a top end 22 of shield 132. Circuit board 152 comprises transmitter 146 and battery 150. Battery 150 is designed to power the components on circuit board 152, transmitter 146, and transducer 130, wherein battery 150 is electrically interconnected to circuit board 152, transmitter 146, and transducer 130.

Figure 5:
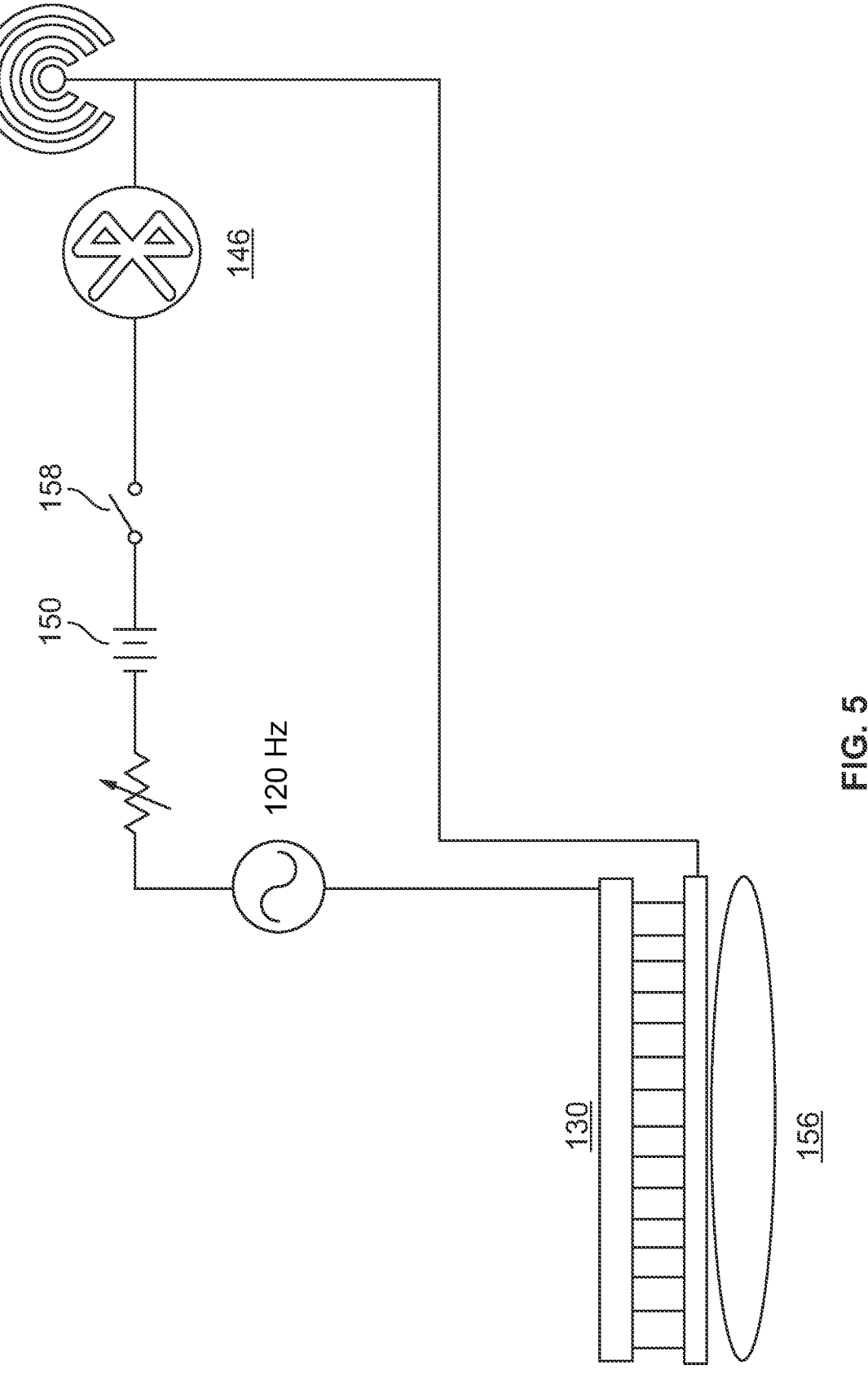
FIG. 5 illustrates a circuit diagram for a transmitter in the chestpiece.

FIG. 5 illustrates a circuit diagram for chestpiece 102 where transducer 130 and transmitter 146 are electrically interconnected on the same circuit. Chestpiece 102 may comprise switch 158 for controlling power to chestpiece 102. In an embodiment, chestpiece 102 comprises switch 158. Once switch 158 is turned on, transducer 130 sends soundwaves out of chestpiece 102. If chestpiece 102 is touching a patient's skin, transducer 130 receives the echoed soundwaves from the patient's skin. After transducer 130 receives the echoed soundwaves from the patient's skin, transmitter 146 wirelessly sends the echoed soundwaves to monitor 104. In embodiments of chestpiece 102 that does not comprise switch 158, transducer 130 will stay on in a lower power mode and will send soundwaves out of chestpiece 102 upon contacting a patient's skin. Then, transducer 130 will wirelessly send the echoed soundwaves to transmitter 146 to be displayed on monitor 104. Both transducer 130 and transmitter 146 receive power from battery 150.

Figure 6:
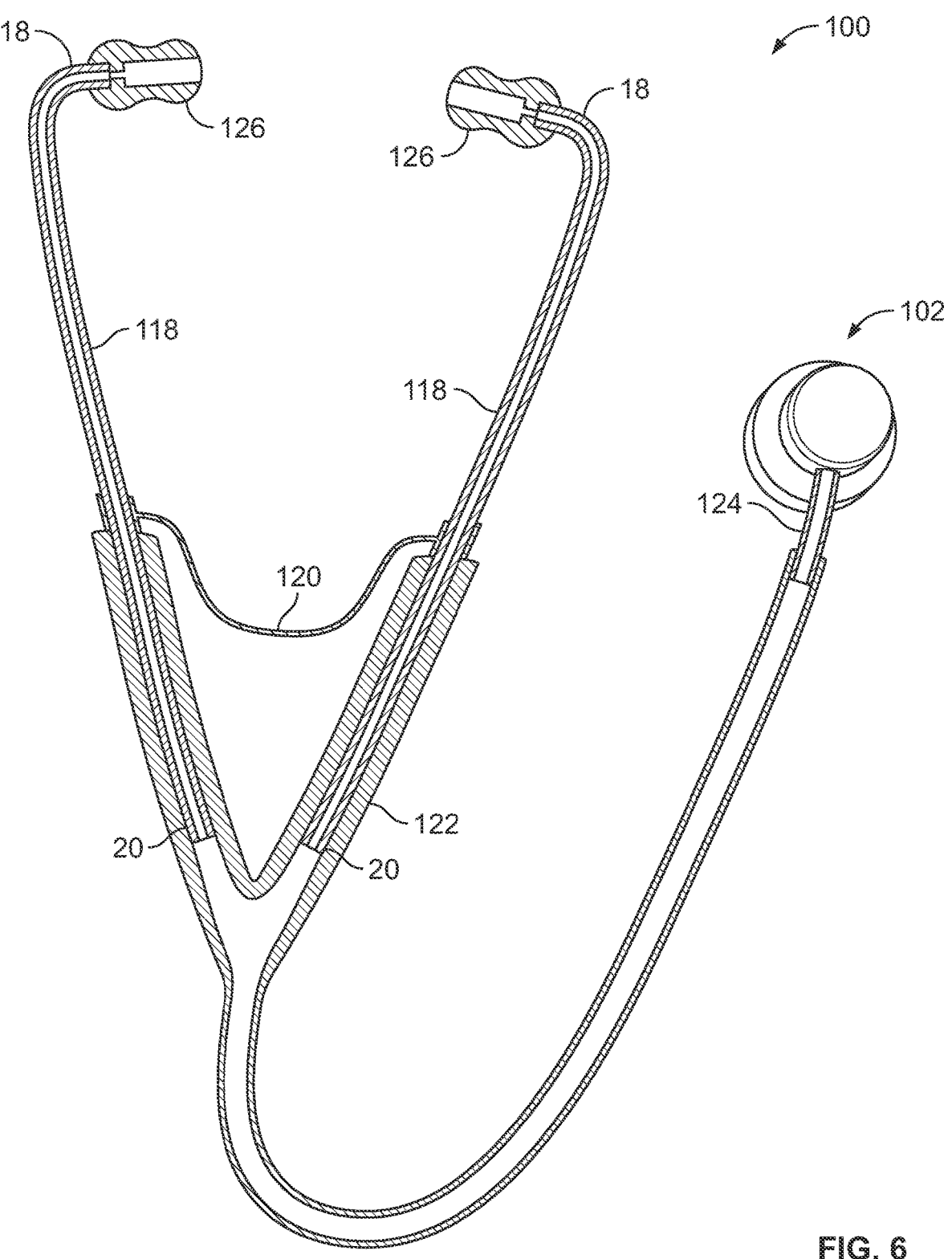
FIG. 6 is a cross-sectional view of the exemplary configuration of the stethoscope in FIG. 1.

FIG. 6 depicts a cross-sectional view of the exemplary configuration of stethoscope 100 in FIG. 1. The view shown in FIG. 6 depicts the connection between parts of stethoscope 100. Specifically, each ear tube 118 comprises a corresponding ear tip 126, wherein each ear tip 126 is attached to top end 18 of each ear tube 118. Furthermore, in one embodiment, ear tubes 118 are connected to binaural spring 120. In addition, tubing 122 envelops bottom end 20 of ear tubes 118 and binaural spring 120. Tubing 122 extends outwardly from bottom end 20 of ear tubes 118.

A method of using stethoscope 100 comprises using chestpiece 102 wherein chestpiece 102 comprises bell 110, diaphragm 116, and housing 114. Housing 114 comprises transducer 130 wherein transducer 130 transmits soundwaves through matching layer 144 to bounce off the patient's skin creating echoed soundwaves. Chestpiece 102 may comprise transmitter 146 wherein transmitter 146 wirelessly transmits the echoed soundwaves from transducer 130 to monitor 104. Further, chestpiece 102 may comprise battery 150 wherein battery 150 powers transmitter 146 and transducer 130.

Thus, specific embodiments of an electronic stethoscope with a sonogram and methods to employ such stethoscope have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. An electronic stethoscope comprising:
i) a pair of ear tubes;
ii) tubing;
iii) a binaural spring; and
iv) a chestpiece, wherein said chestpiece comprises:
    a bell;
    a drum;
    a diaphragm located on a bottom side of said chestpiece;
    a stem;
    a circuit board;
    a housing, and
    a switch,
    wherein:
    said bell is connected to a top end of said drum;

said stem is attached to a curved side of said drum;

a bottom end of said drum is connected to a top end of said housing;

said housing comprises a transducer, wherein said transducer comprises a shield;

said transducer is electrically interconnected to said circuit board;

said circuit board comprises a battery and a transmitter, wherein said battery and said transmitter are electrically interconnected to said circuit board;

said circuit board is connected to a top end of said shield; and said stem is connected to said tubing, wherein said binaural spring is connected to a bottom end of said pair of ear tubes;

said tubing envelops said bottom end of said pair of ear tubes and said binaural spring;

wherein said switch is configured to control power to said circuit board; and wherein said diaphragm comprises a plurality of stationary and unmanipulable soundwave holes located on said bottom side of said chestpiece.

2. The electronic stethoscope of claim 1, wherein said chestpiece is configured to:

produce soundwaves from said transducer that are sent through said plurality of soundwave holes to a patient's skin;

receive echoed soundwaves that are echoed off said patient's skin; and transmit said echoed soundwaves through said transmitter to a monitor.

3. The electronic stethoscope of claim 1, wherein said transducer further comprises an acoustic insulator and a piezoelectric element.

4. The electronic stethoscope of claim 1, wherein said transmitter is a Bluetooth transmitter.

5. The electronic stethoscope of claim 1, wherein said chestpiece comprises a lens for the purpose of assisting the output of the soundwaves.

6. A method of using an electronic stethoscope comprising:

applying a gel on a patient's skin;

producing soundwaves from a transducer, wherein said transducer is electrically connected to a circuit board and a battery located inside a chestpiece, wherein said soundwaves are sent to said patient's skin;

receiving echoed soundwaves from said patient's skin; and transmitting said echoed soundwaves through a transmitter to a monitor, wherein said transmitter is electrically interconnected to said circuit board and said battery is located inside said chestpiece; and wherein said electronic stethoscope comprises:

a pair of ear tubes;

tubing;

a binaural spring, wherein said chestpiece comprises:

i) a bell;

ii) a drum;

iii) a stem; and iv) a housing, wherein:

said bell is connected to a top end of said drum;

said stem is attached to a curved side of said drum;

a bottom end of said drum is connected to a top end of said housing; said housing comprises said transducer, wherein said transducer comprises a shield; and said circuit board is connected to a top end of said shield, wherein:

said stem is connected to said tubing;

said binaural spring is connected to a bottom end of said pair of ear tubes;

said tubing envelops said bottom end of said pair of ear tubes and said binaural spring; and wherein a bottom side of said chestpiece comprises a diaphragm and said diaphragm comprises a plurality of stationary and unmanipulable soundwave holes.

7. The method of using an electronic stethoscope of claim 6, wherein said soundwaves that are produced from said transducer pass through said plurality of stationary and unmanipulable soundwave holes before reaching said patient's skin.

8. The method of using an electronic stethoscope of claim 6, wherein said transmitter is a Bluetooth transmitter.

9. The method of using an electronic stethoscope of claim 6, wherein said chestpiece comprises a lens for the purpose of assisting the output of the soundwaves.

10. The method of using an electronic stethoscope of claim 6, wherein said chestpiece comprises a switch, wherein said switch is configured to control power to said circuit board.

11. An electronic stethoscope comprising:

i) a pair of ear tubes;

ii) tubing;

iii) a binaural spring; and iv) a chestpiece, wherein said chestpiece comprises:

a bell;

a drum;

a diaphragm located on a bottom side of said chestpiece;

a stem;

a circuit board; and a housing, wherein:

said bell is connected to a top end of said drum;

said stem is attached to a curved side of said drum;

a bottom end of said drum is connected to a top end of said housing;

said housing comprises a transducer, wherein said transducer comprises a shield, an acoustic insulator, and a piezoelectric element;

said transducer is electrically interconnected to said circuit board;

said circuit board comprises a battery and a transmitter, wherein said battery and said transmitter are electrically interconnected to said circuit board;

said circuit board is connected to a top end of said shield, and said diaphragm further comprises a plurality of stationary and unmanipulable soundwave holes located on said bottom side of said chestpiece, wherein:

said stem is connected to said tubing;

said binaural spring is connected to a bottom end of said pair of ear tubes; said ear tubes comprise a corresponding ear tip; and said tubing envelops said bottom end of said pair of ear tubes and said binaural spring.

12. The electronic stethoscope of claim 11, wherein said chestpiece is configured to:

produce soundwaves from said transducer that are sent through said plurality of soundwave holes to a patient's skin; and receive echoed soundwaves that are echoed off said
  patient's skin; and
transmit said echoed soundwaves through said transmitter
  to a monitor.

* * * * *